United States Patent [19]

Blake, III et al.

[11] Patent Number: 5,242,400
[45] Date of Patent: Sep. 7, 1993

[54] DISPOSABLE PRE-FILLED SYRINGE WITH RETRACTABLE NEEDLE

[75] Inventors: Joseph W. Blake, III, New Canaan; Thomas E. Sloane, Jr., West Redding, both of Conn.; Laurence Wesser, Nazareth, Pa.

[73] Assignee: The Medtech Group, Inc., South Plainfield, N.J.

[21] Appl. No.: 804,091

[22] Filed: Dec. 6, 1991

[51] Int. Cl.$^5$ ............................................. A61M 5/32
[52] U.S. Cl. ................................. 604/110; 604/195; 604/240; 604/220
[58] Field of Search ............... 604/110, 192, 195, 197, 604/198, 263, 218, 228, 220, 187

[56] References Cited

U.S. PATENT DOCUMENTS

| | | | |
|---|---|---|---|
| 2,671,450 | 3/1954 | Dann | 604/192 |
| 2,688,963 | 9/1954 | Smith | 604/192 |
| 3,865,236 | 2/1975 | Nycroft | 604/192 |
| 4,747,830 | 5/1988 | Gloger et al. | 604/110 |
| 4,790,822 | 12/1988 | Haining | 604/110 |
| 4,947,863 | 8/1990 | Haber et al. | 604/198 |
| 4,961,730 | 10/1990 | Ponez | 604/198 |
| 4,964,866 | 10/1990 | Szware | 604/192 |
| 4,986,813 | 1/1991 | Blake, III et al. | 604/195 |
| 5,026,345 | 6/1991 | Teringo | 604/110 |
| 5,084,017 | 1/1992 | Mafletone | 604/110 |

FOREIGN PATENT DOCUMENTS

| | | | |
|---|---|---|---|
| 2646086 | 10/1990 | France | 604/228 |
| 2654629 | 5/1991 | France | 604/110 |
| 9003816 | 4/1990 | World Int. Prop. O. | 604/228 |

Primary Examiner—C. Fred Rosenbaum
Assistant Examiner—Manuel Mendez
Attorney, Agent, or Firm—Arthur L. Plevy

[57] ABSTRACT

A pre-filled hypodermic syringe includes a retractable needle and detachable plunger shaft so the syringe can be selectively rendered inoperable. A liquid held within the syringe is held in place by a elastomeric stop that surrounds the discharging tip of the needle. When the syringe is to be used, the needle stop is removed and the plunger is advanced within the syringe barrel until the liquid is displaced through the needle. When the plunger contacts the base of the needle within the syringe barrel, the plunger becomes capable of being rotated. The rotation of the plunger connects the plunger to the needle and the needle can be retracted into the syringe barrel with the plunger. Once fully retracted, the needle cants and the plunger shaft can be destructively disconnected from the plunger, rendering the syringe inoperable.

19 Claims, 4 Drawing Sheets

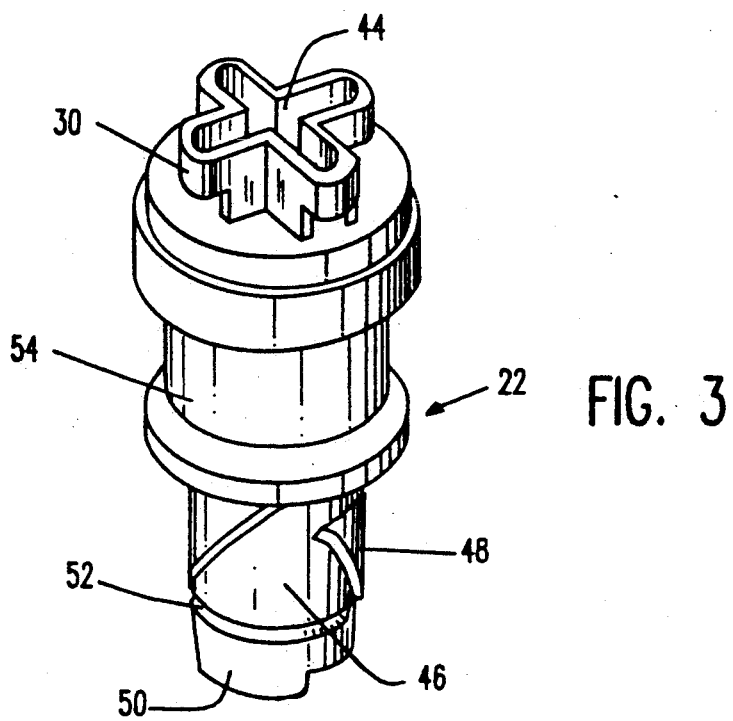
FIG. 3
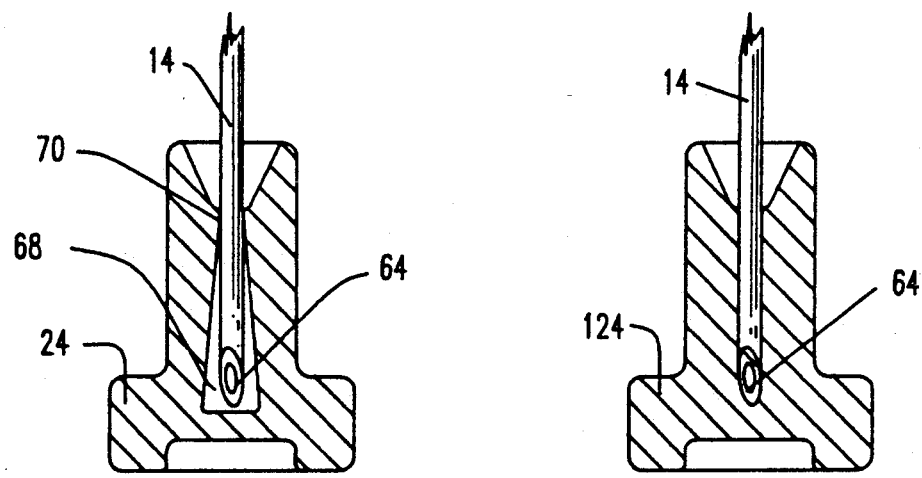
FIG. 4
FIG. 5

5,242,400

DISPOSABLE PRE-FILLED SYRINGE WITH RETRACTABLE NEEDLE

FIELD OF THE INVENTION

The present invention relates to a disposable hypodermic syringe having a retractable needle and, more particularly, to such disposable syringes where both the needle and the plunger shaft are selectively rendered inoperable.

BACKGROUND OF THE INVENTION

To prevent transmission of blood borne diseases it has become standard medical practice to use a syringe once, then dispose of it in an acceptable manner. In the industrial world it has been determined that the reuse of a syringe is neither safe nor economical. Consequently, syringes are disposed of daily from such sources as hospitals, clinics, doctors' offices, dentists, and other health care organizations. Since syringes are contaminated with a patient's blood, syringes have the potential to carry with them the diseases of the patient, such as AIDS, Hepatitis, or other dangerous diseases present in a patient's blood. Thus, many unwary health workers and medical waste disposal personnel can be accidentally pricked by these contaminated syringe needles. Unfortunately, contaminated syringes are not always disposed of properly and have been found washed up on beaches or tossed into ordinary trash, where any unfortunate person in proximity of the syringes may be accidentally pricked. Such accidental syringe needle sticks, therefore, create a large health risk not only to healthcare professionals, but also to the general populous.

Another unfortunate consequence of syringe disposal mismanagement is the acquisition and use of syringes by intravenous drug users. Because of the unavailability of new sterile syringes, drug users often reuse the same syringe and needle many times and share the syringe with other drug users. This pattern of syringe use spreads life-threatening diseases throughout the drug using community.

To eliminate the problems of accidental syringe needle sticks, many syringe designs have been created to retract the needle into the body of the syringe after its use. By retracting the needle, the point of the needle is shielded and thus the danger of an accidental prick is removed. Such needle retraction devices are exemplified in U.S. Pat. Nos. 4,955,869 to Bin, 4,643,199 to Jennings, Jr. et al, and 4,507,117 to Vining et al.

To prevent both the problems of accidental needle sticks and repeated use by drug users, many syringe designs have been created whereby the needle is retracted into the syringe barrel and the functionality of the syringe is compromised after a single use. Such syringes may lock the syringe piston in its retracted position, have a breakaway piston shaft, or both, which prevent the syringe's reuse. Such syringe designs are shown in U.S. Pat. Nos. 4,826,484 to Haber et al, 4,790,822 to Haining, 4,747,830 to Gloyer et al, 4,650,468 to Jennings, Jr., 4,562,844 to Carpender et al and 4,026,287 to Haller. All of these references use locking devices that greatly increase the complexity of manufacturing the syringe, thus resulting in syringes that are significantly more expensive than the typical syringe without a safety design.

An alternative safety feature, used to render hypodermic syringes inoperative after one use, is to cant the needle after it is retracted into the syringe barrel. By canting the needle, the needle contacts the inside of the syringe, thus acting as its own safety lock. Such syringe designs are shown in U.S. Pat. Nos. 4,986,813 to Blake, III et al and 4,770,655 to Haber et al. In any event, it is desirable to have such safety features while providing a reliable operating device capable of manufacture at competitive prices.

It is, therefore, an object of the present invention to provide an improved safety hypodermic syringe that selectively renders both the piston shaft and the needle inoperable, and does so in a manner that minimizes both the cost and complexity of manufacturing the syringe.

SUMMARY OF THE INVENTION

In accordance with the present invention, a safety hypodermic syringe, which may be pre-filled with medication, is disclosed. The syringe comprises a syringe barrel, containing a volume of medicated liquid and a retractable needle. A plunger displaces the liquid within the syringe through the needle. Prior to the use of the syringe, the liquid is prevented from flowing through the needle by the presence of a stop grommet positioned around the discharging end of the needle. The plunger is driven by a removable shaft. The shaft can also be used to rotate the piston; however, the shaft is limited in its rotation by the presence of a stop tab that engages the shaft as it turns. A relief is formed on the shaft that clears the stop tab. The relief is positioned on the shaft so that the relief aligns with the stop tab when the plunger contacts the retractable needle. By rotating the plunger, as the plunger is contacting the retractable needle, the plunger couples with the retractable needle. Consequently, the needle can now be retracted into the syringe barrel by retreating the plunger into the syringe barrel. Prior to the engagement of the needle to the plunger, the stop tab assures that the plunger does not become misaligned by the premature rotation of the shaft.

After the needle is retracted, the shaft is pulled out of the syringe barrel and away from the plunger. When the shaft is removed, the coupling between the plunger and shaft is disabled, preventing any re-attachment. Additionally, the needle, when retracted, cants in the syringe barrel. The combination of the canted needle and the disabled shaft ensures the syringe cannot be reused.

BRIEF DESCRIPTION OF THE DRAWINGS

For a better understanding of the present invention, reference is made to the following description of an exemplary embodiment thereof, considered in conjunction with the accompanying drawings, in which:

FIG. 3 is an enlarged perspective view of the plunger used within the exemplary embodiment of the present invention;

FIG. 4 is an enlarged partially cross-sectioned view of one preferred embodiment of the needle stop segment of the present invention;

FIG. 5 is an enlarged partially cross-sectioned view of an alternative preferred embodiment of the needle stop segment of the present invention.

DETAILED DESCRIPTION OF THE DRAWINGS

Figure 1:
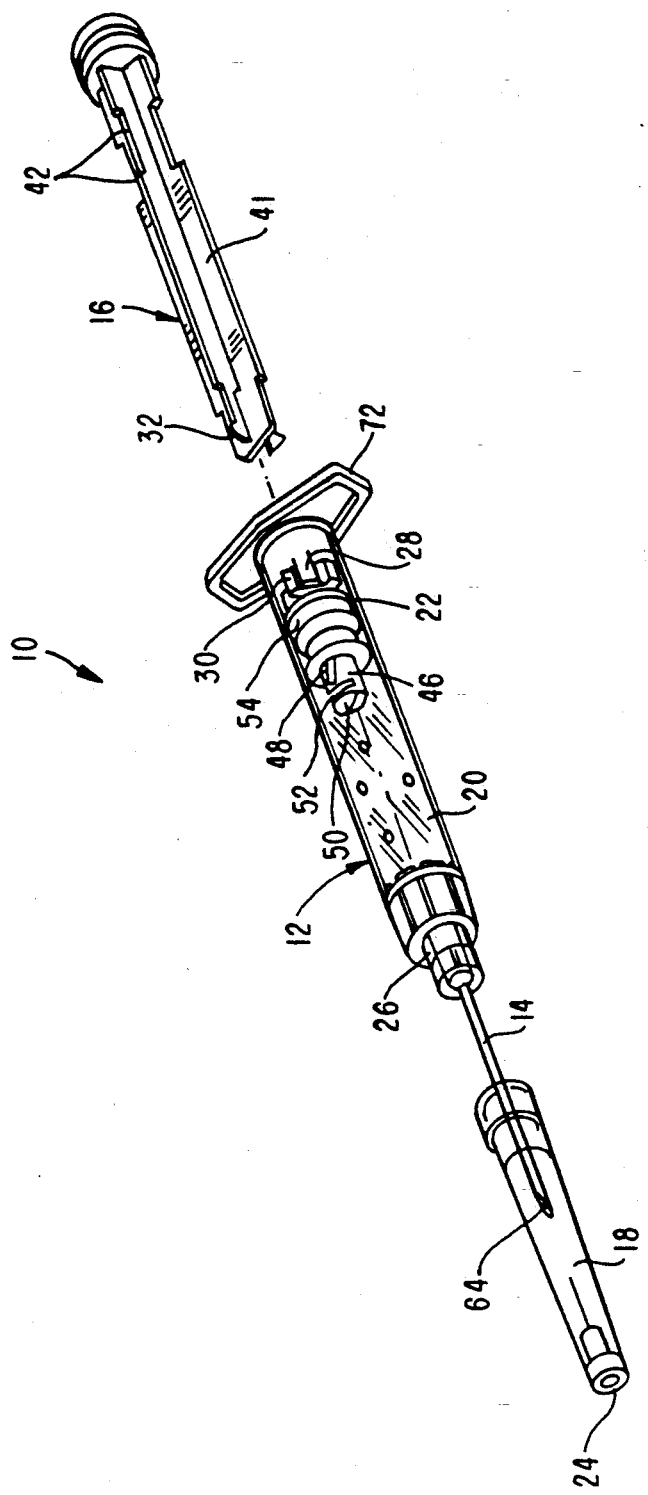
FIG. 1 is a perspective view of a hypodermic syringe constructed in accordance with one exemplary embodiment of the present invention; the hypodermic syringe being shown in a partially exploded fashion to facilitate consideration and discussion.

Referring to FIG. 1, a disposable, one-time use, hypodermic syringe 10 is shown. The syringe 10 includes a syringe barrel 12 having a needle 14 extending from one end, covered by a needle cap 18, and a plunger shaft 16 positioned at the opposite end. The syringe barrel 12 is filled with a predetermined volume of a liquid 20. The liquid may be a typical fluid medication or other liquid, injectable substance as vitamins, minerals, and so on. The liquid 20 is prevented from flowing out of the syringe barrel 12 by the presence of the plunger 22 obstructing the open end of the syringe barrel 12 and the elastomeric stop 24 obstructing the lumen of the needle 14. The stop 24 is positioned as part of the needle cap 18. The stop 24 engages the needle 14 when the needle cap 18 is placed over the needle 14 and the needle cap 18 is placed around the neck 26 of the syringe barrel 12.

The plunger 22 is prevented from leaving the open end of the syringe barrel 12 by the presence of lock tabs 28 that protrude inwardly from the inside walls of the syringe barrel 12. A female coupling 30 is formed at one end of plunger 22. Locking fingers 32 are formed at the end of the plunger shaft 16 which fit through, and engage, the female coupling 30.

When manufactured, the present invention syringe 10 may be packaged either with the plunger shaft 16 already attached to the plunger 22 or may be packaged with the plunger shaft separate from the plunger 22. Preferably, the syringe 10 is packaged with the plunger shaft 16 not connected to prevent the plunger 22 from being accidentally contacted during handling. Accidental contact with the plunger 22 may displace liquid 20 through the needle 14, dislodging the elastomeric stop 24 and prematurely releasing the liquid 20.

Figure 2:
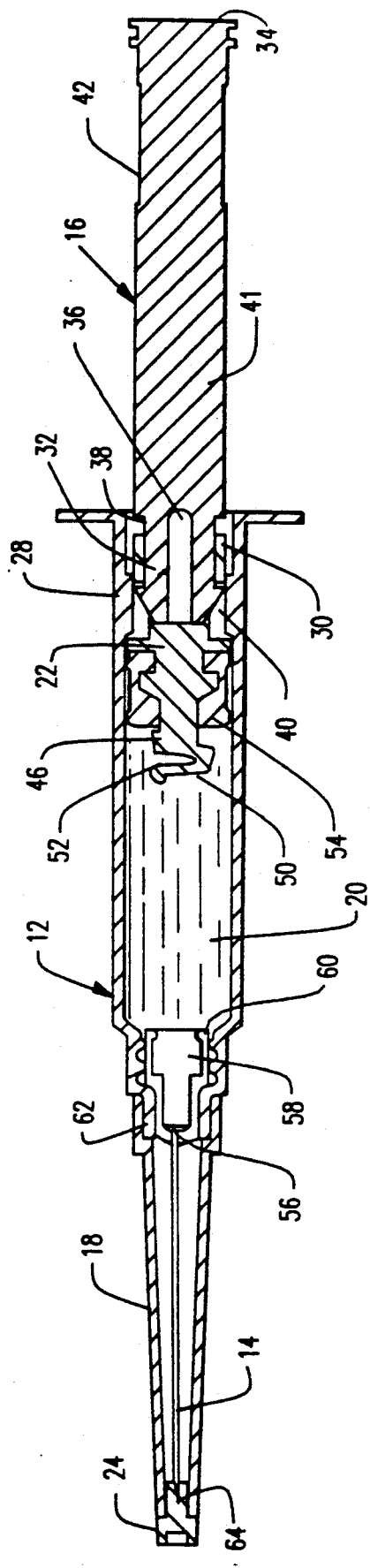
FIG. 2 is a cross-sectional view of the exemplary embodiment of the present invention as it would appear prior to use.
Figure 6:
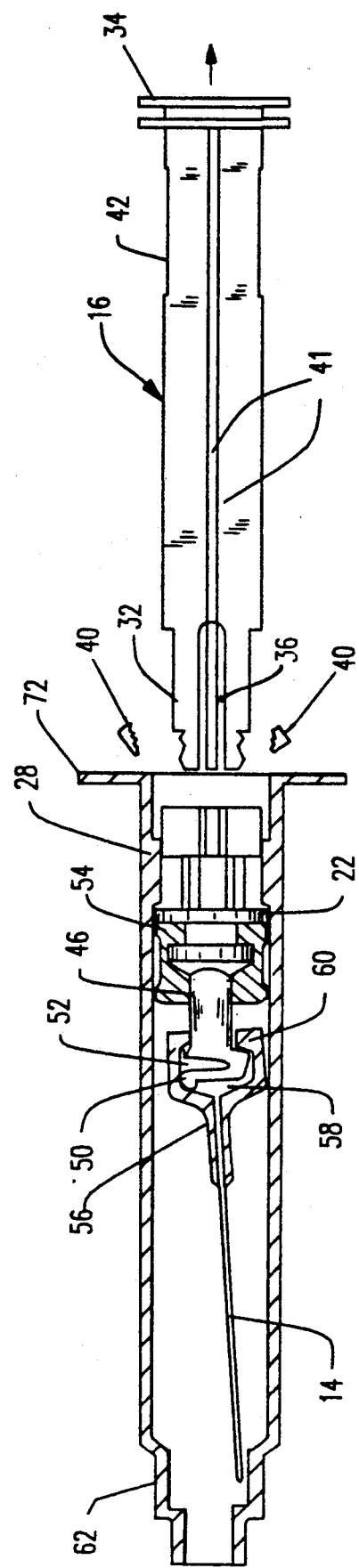
FIG. 6 is a partially cross-sectioned view of the exemplary embodiment of the present invention as it would appear after use and having its safety features engaged.

Referring to FIG. 2, the interconnection of the needle cover 18, syringe barrel 12 and plunger shaft 16 are detailed. Beginning with the plunger shaft 16, a thumb press 34 is formed at the end of the piston shaft 16 opposite the locking fingers 32. The locking fingers 32 are separated by a gap space 36 that permits the locking fingers 32 to deform inwardly. A relief 38 is formed along each locking finger 32, opposite the gap space 36. The relief 38 creates a shearing tab 40 at the ends of each locking finger 30. The locking fingers 32 are deformed inwardly and passed through the female coupler 30. The shearing tabs 40 return to their original position as the body of the female coupler 30 passes into the reliefs 38 on each locking finger 32. Once in position, the abutment of the shearing tabs 40 against the female coupler 30 prevents the plunger shaft 16 from being pulled out of the female coupler 30. The female coupler 30 has a cross-shaped aperture 44 formed through it to accept the cross-shape of the plunger shaft 16 created by the four radially disposed flanges 41 (see FIG. 3). Consequently, once the flanges 41 of the plunger shaft 16 pass into the female coupler 30, any longitudinal axis rotation of the plunger shaft 16 is directly transferred to the female coupler 30.

The locking tabs 28, that prevent the plunger from being pulled out of the syringe barrel 12 by the plunger shaft 16, also interfere with the ability of the female coupler 40 to rotate. As such, the arc through which the female coupler 40 can be rotated by the piston shaft 16 is limited by the dimensions of the female coupler 40 and the position and number of locking tabs 28.

The female coupler 40 is integrally formed as part of the plunger 22. Referring to FIGS. 2–3, it can be seen that the plunger 22 has a complex shape. The end of the plunger 22, opposite the female coupler 40, is shaped to create an engagement hub 46. The engagement hub 46 has lock wedges 48 formed on it and terminates in an uneven tip 50 partially separated from the remainder of the engagement hub 46 by a spring relief 52. An elastic grommet 54 surrounds the middle portion of the plunger 22, creating a liquid impermeable seal around the interior walls of the syringe barrel 12.

At the opposite end of the syringe barrel 12 is positioned a retractable needle base 56, that supports the needle 14. The needle base 56, facing the piston 22, is shaped to form a hub receptacle 58. Inwardly facing catch locks 60 are formed inside the hub receptacle 58. The needle base 56 is surrounded by a syringe neck 62 that forms the distal end of the syringe barrel 12. The needle base 56 creates a liquid impermeable seal against the syringe neck 62.

The needle 14, protruding from the syringe barrel 12, is covered by a hollow needle cap 18. The end of the needle cap 18 is sealed with an elastomeric stop 24. As the needle cap 18 is placed over the needle 14, the sharpened tip 64 of the needle 14 contacts the stop 24.

Referring to FIGS. 4 and 5, two embodiments of the elastomeric stop 24 are shown. In FIG. 4, a pocket 68 is formed about the tip 64 of the needle 14. The pocket 68 narrows to create a seal 70 around the needle 14. Consequently, the needle tip 64 avoids contact with the stop 24.

In FIG. 5, an alternative stop 124 is shown, wherein the tip 64 of the needle 14 is forced into the material of the stop 124, cutting its own channel as it is advanced. This embodiment is easier and cheaper to create, but has the disadvantage of contacting the needle tip 64.

By referring now to FIGS. 1–4, the operation of injecting a patient with the present invention hypodermic syringe 10 is detailed. If the hypodermic syringe 10 is packaged with the plunger shaft 16 separate from the plunger 22, the person using the syringe 10 inserts the plunger shaft 16 into the plunger 22. To use the hypodermic syringe 10, the needle cap 18 is then removed. By removing the needle cap 18, the elastomeric stop 24 is removed from the tip 64 of the needle 14, and the lumen of the needle 14 is clear from the syringe barrel 12 to the needle tip 64. The needle 14 is then inserted into a patient and the plunger shaft 16 is driven into the syringe barrel 12 by applying opposing pressures to the thumb rest 32 and the finger rests 70. The plunger shaft 16 drives the plunger 22 deeper into the syringe barrel 12, displacing the fluid 20 out through the needle 14. The displacement continues until the plunger engagement hub 46 enters the needle hub receptacle 58. Once in the receptacle 58, the plunger shaft 16 is rotated. The plunger shaft 16 rotation is transferred to the engagement hub 46, via the female coupler 30. By rotating the engagement hub 46, the lock wedges 48 on the engagement hub 46, engage the catch locks 60 positioned within the hub receptacle 58. The lock wedges 48 drive the engagement hub 46 further into the receptacle 56 until the hub tip 50 strikes the floor of the receptacle 56 and the spring relief 52 is compressed. The passage of the lock wedges 48, on the engagement hub 46, under the catch looks 60 of the lock wedges 48 integrally connects the plunger 22 to the needle 14.

Lock tabs 28 extend inwardly from the syringe barrel 12 preventing the removal of the plunger 22 from the syringe barrel 12. The lock tabs 28 also interfere with the rotation of the plunger shaft 16 by abutting against the flanges 41 that depend from the plunger shaft 16. Shaft reliefs 42 are formed on the flanges 41 of the plunger shaft 16. When the shaft reliefs 42 pass under the lock tabs 28 there is no interference and the plunger shaft 16 is free to rotate. When the engagement hub 46 of the plunger 22 enters the needle base receptacle 56, the plunger shaft 16 must be rotated to engage the plunger 22 to the needle base receptacle 56. As such, the shaft reliefs 42 are formed on the flanges 41 of the piston shaft 16 in a position that places the shaft reliefs 42 under the lock tabs 28, as the engagement hub 46 of the plunger 22 enters the needle base receptacle 56. Such a positioning of the shaft reliefs 42 on the flanges 41 of the plunger shaft 16 allows the plunger shaft 16 to be rotated, thus engaging the plunger 22 to the needle base receptacle 56. The presence of the locking tabs 28, preventing the rotation of the plunger 22 until the plunger 22 contacts the needle base receptacle 56, also help guide the engagement hub 46 into the needle base receptacle 56. The locking tabs 28 prevent the premature rotation of the engagement hub 46 into the needle base receptacle 56.

With the engagement hub 46 coupled to the needle hub receptacle 58, the plunger shaft 16 is withdrawn from the syringe barrel 12. The movement of the plunger shaft 16 is transferred to the needle base 56, consequently, the needle 14 is drawn into the syringe barrel 12. As the needle 14 clears the neck 62 of the syringe barrel 12, the bias created by the compression of the spring relief 52 on the needle base 56 causes the needle base 56 to shift or cant to one side. Consequently, when the needle 14 is no longer supported by the syringe barrel neck 62, the needle 14 cants to one side within the syringe barrel 12. The canting of the needle 14 from its original axial orientation prevents it from being returned back through the syringe barrel neck 62.

The plunger shaft 16 is retracted within the syringe barrel 12 until the plunger 22 contacts the locking tabs 28, and the plunger 22 is forced to stop. By continuing the retracting force on the plunger shaft 16, the shear tabs 40 are stressed against the edge of the female coupler 30. When a large enough retracting force is applied, the shear tabs 40 will break off the plunger shaft 16, and the plunger shaft 16 will be disconnected from the plunger 22.

The needle 14 being canted within the syringe barrel 12, prevents the plunger 22 from being advanced. The shearing of the shear tabs 40 prevents the plunger 22 from being retracted out of the syringe barrel 12. Consequently, the hypodermic syringe 10 is rendered entirely functionless and can be disposed of without fear of reuse or danger of an accidental needle stick.

It will be understood that the embodiment described herein is merely exemplary and that a person skilled in the art may make variations and modifications without departing from the spirit and scope of the invention. More specifically, many devices are known in the art for retaining a plunger in a syringe, coupling a plunger to a retractable needle and the canting of a retracted needle. All such variations and modifications are intended to be included within the scope of the invention as defined in the appended claims.

We claim:

1. A hypodermic syringe comprising:
 a substantially cylindrical syringe barrel symmetrically disposed about a longitudinal axis and having an open proximal end, and a substantially closed distal end;
 a retractable hollow needle terminating within said syringe barrel at a base support and extending through said distal end along said longitudinal axis to a sharpened discharging tip;
 a plunger, axially and reciprocally movable through said syringe barrel, said plunger having an engagement means thereon that enters said base support of said needle as said plunger is advanced to said distal end of said syringe barrel, said engagement means engaging said base support when rotated around said longitudinal axis relative said base support, whereby said engagement means operates to retract said needle into said syringe barrel and cants said needle relative said longitudinal axis within said syringe barrel; and
 an obstructing means for obstructing said plunger, wherein said plunger is prevented from rotating about said longitudinal axis within said syringe barrel after said needle is retracted, thereby preventing said engagement means from detaching from said needle base.

2. The syringe of claim 1, wherein said plunger includes a plunger head, a removable plunger drive means for axially and reciprocally moving said plunger head in said syringe barrel, a coupling means for joining said plunger head to said plunger drive means, and a disabling means for disabling said coupling means when said plunger drive means is removed from said plunger head.

3. The syringe of claim 2, wherein said obstructing means prevents said plunger head from exiting said syringe barrel through said open proximal end.

4. The syringe of claim 3, wherein the cant of said needle within said syringe barrel prevents said plunger head from being again advanced to said distal end of said syringe barrel.

5. The syringe of claim 1, further including a predetermined volume of liquid contained within said syringe barrel and a flow restriction means disposed on said discharging tip of said needle for preventing the flow of said liquid through said needle.

6. The syringe of claim 5, wherein said flow restriction means is an elastomeric stop and said stop has a large inner cavity accessed by a smaller aperture wherein said discharging tip is passed through said aperture into said inner cavity whereby said stop creates a liquid impermeable seal around said needle proximate said discharging tip, without contacting said discharging tip.

7. The syringe of claim 5, wherein said stop is part of a larger needle cap that surrounds said needle, isolating said needle from the surrounding environment.

8. The syringe of claim 2, wherein said disabling means includes at least one locking tab on said plunger drive means that engages said plunger head, said at least one locking tab destructively breaking from said plunger drive means, allowing said plunger drive means to separate from said plunger head when a retracting force is applied to said plunger drive means, biasing said plunger drive means out of said proximal end of said barrel along said longitudinal axis, wherein said force is in excess of a predetermined maximum value.

9. The syringe of claim 3, wherein said plunger drive means is a shaft having a plurality of flanges extending outwardly along the longitudinal axis of said shaft, said shaft terminating at a thumb rest at the end opposite said coupling means.

10. The syringe of claim 9, wherein said coupling means includes a spring biased locking tab disposed on at least one of said flanges at the end of said shaft opposite said thumb pad, and a shaft receptacle disposed on said plunger head for the passage of said spring biased locking tab therethrough, said shaft receptacle including at least one recessed area wherein said spring biased locking tab expands, preventing the non-destructive withdrawal of said shaft from said shaft receptacle.

11. The syringe of claim 10, wherein said locking tab has a predetermined shear point at which said locking tab shears away from said flange.

12. The syringe of claim 11, wherein said disabling means is an abutment of said locking tab against said shaft receptacle within said recessed area, said abutment applying a shear force to said locking tab in excess of said shear point when a predetermined minimum retracting force is applied to said shaft that biases said shaft out of said shaft receptacle.

13. The syringe of claim 9, wherein said obstructing means includes at least one protrusion extending inwardly from said syringe barrel.

14. The syringe of claim 13, wherein said at least one protrusion interferes with the rotation of said plunger drive means when said needle is retracted within said syringe barrel.

15. The syringe of claim 14, wherein a relief is formed on plunger drive means such that when said at least one protrusion is positioned over said relief, said at least one protrusion does not interfere with said plunger drive means and said plunger drive means is free to rotate.

16. The syringe of claim 15, wherein said relief is positioned on said plunger drive means at a predetermined position so that said at least one protrusion is positioned over said relief as said plunger engages said needle at said distal end of said syringe barrel.

17. A hypodermic syringe, comprising:
a syringe barrel having an open proximal end and a substantially closed distal end;
a retractable needle assembly extending through said distal end of said syringe barrel;
a plunger, axially and reciprocally movable through said syringe barrel and having an engagement means thereon for engaging said needle assembly at said distal end of said syringe barrel and retracting said needle assembly into said syringe barrel as said plunger is retracted toward said proximal end of said syringe barrel, wherein said engagement means engages said needle assembly upon the rotational movement of said plunger relative said needle assembly at said distal end;
a plunger drive means for driving said plunger between said distal end and said proximal end and rotating said plunger in said syringe barrel; and
a stop means for preventing said plunger from exiting said syringe barrel through said proximal end, said stop means engaging said plunger drive means when said needle assembly is retracted into said syringe barrel whereby said stop means prevents the rotation of said plunger drive means within said barrel and prevents said plunger from disengaging from said needle assembly.

18. The syringe of claim 17, wherein a relief is disposed on said plunger drive means, whereby said stop means corresponds in position with said relief when said plunger is at said distal end of said syringe barrel and said plunger drive means is free to rotate.

19. The syringe of claim 17, wherein said plunger drive means includes at least one shear tab that engages said plunger and joins said plunger drive means to said plunger, said at least one shear tab shearing off said plunger drive means, disengaging said drive means from said plunger as said plunger is biased against said stop mens by said plunger drive means with a predetermined force.

* * * * *